(12) United States Patent
Freeman et al.

(10) Patent No.: US 6,811,663 B1
(45) Date of Patent: Nov. 2, 2004

(54) MICROELECTRODE SYSTEM

(75) Inventors: Neville John Freeman, Tarporley (GB); Andrew Mount, Edinburgh (GB)

(73) Assignee: Sensorflex Limited (GB)

( * ) Notice: Subject to any disclaimer, the term of this patent is extended or adjusted under 35 U.S.C. 154(b) by 0 days.

(21) Appl. No.: 09/700,649

(22) PCT Filed: May 18, 1999

(86) PCT No.: PCT/GB99/01379
§ 371 (c)(1),
(2), (4) Date: May 21, 2001

(87) PCT Pub. No.: WO99/60392
PCT Pub. Date: Nov. 25, 1999

(30) Foreign Application Priority Data

May 18, 1998 (GB) ............................................. 9810568

(51) Int. Cl.[7] ..................... G01N 27/30; G01N 27/327; G01N 27/333; G01N 27/453; G01N 27/02
(52) U.S. Cl. ..................... 204/400; 204/600; 204/612; 204/403.01; 204/409; 204/424; 324/448; 324/449
(58) Field of Search ............................... 204/600, 612, 204/400, 403.01, 403.03, 403.04, 403.05, 403.13, 409, 410, 411, 424, 284; 324/448, 449

(56) References Cited

U.S. PATENT DOCUMENTS

| | | | |
|---|---|---|---|
| 4,647,362 A | * | 3/1987 | Watanabe ................... 204/411 |
| 4,666,574 A | | 5/1987 | Oda et al. |
| 5,314,604 A | * | 5/1994 | Friese et al. ................ 204/410 |
| 5,393,401 A | * | 2/1995 | Knoll ..................... 204/403.06 |
| 5,727,977 A | * | 3/1998 | Maracas et al. .............. 445/24 |
| 5,824,494 A | | 10/1998 | Feldberg |

FOREIGN PATENT DOCUMENTS

| | | |
|---|---|---|
| DE | 25717809 | 4/1998 |
| DE | 19645653 | 5/1998 |
| EP | 0585933 | 3/1994 |
| JP | 0102042 | 3/1984 |
| JP | 06-324015 A | * 11/1994 |
| JP | 09-021778 A | * 1/1997 |
| WO | WO 93/22678 | 11/1993 |
| WO | 9724600 A1 | * 7/1997 |

OTHER PUBLICATIONS

JPO computer translation of Fukuda (JP 06–324015 A).*
JPO computer translation of Toyama et al. (JP 09–021778 A).*

* cited by examiner

Primary Examiner—Alex Noguerda
(74) Attorney, Agent, or Firm—Factor & Lake

(57) ABSTRACT

A microelectrode system suitable for use in preparative and analytical chemistry having a laminated structure with one or more apertures. In one embodiment a microelectrode system (1) comprises alternating layers of conductor (3) and dielectric (or insulator) (4). The laminated structure (2) comprises two conductor layers (3) and two dielectric layers (4) formed on a base (5) of silicon or a polymeric material. The conducting layers (3) form electrodes in the microelectrodes system (1). The laminated structure has formed within it an aperture in the form of a well (6) being open at one end (7) and closed at the opposite end (8). In another embodiment, the apertures take the form of through holes.

20 Claims, 5 Drawing Sheets

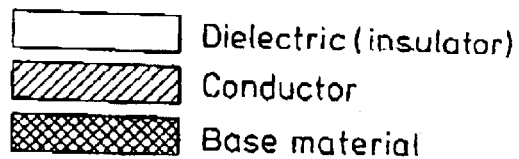
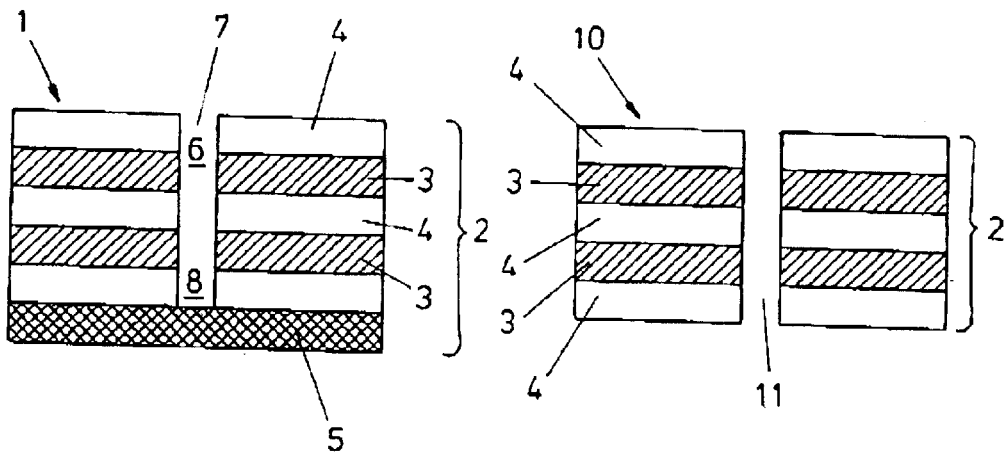
FIG. 1a  FIG. 1b
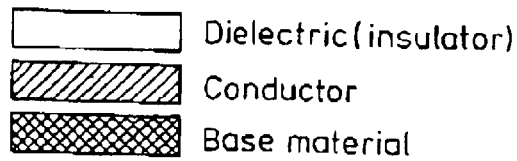
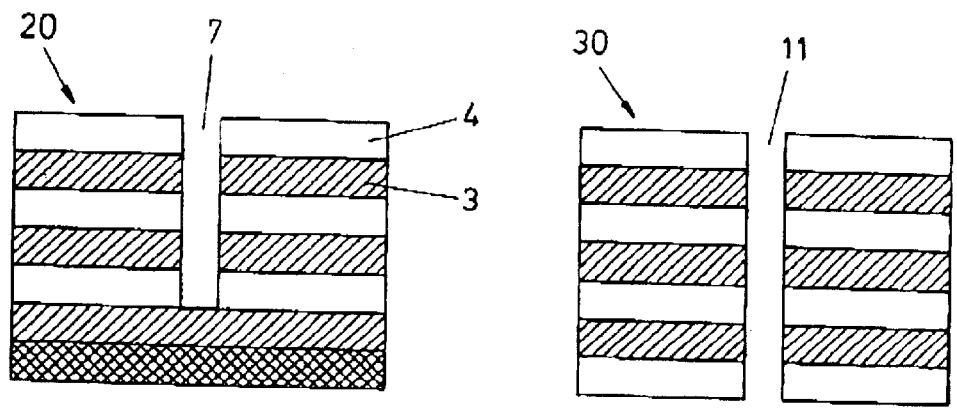
FIG. 2a  FIG. 2b

□ Dielectric (insulator)
▨ Conductor
▩ Base material
▨ Reagent loaded or functional dielectric

MICROELECTRODE SYSTEM

The present invention relates to an electrode system, and particularly to a microelectrode system suitable for use in preparative and analytical chemistry.

Microelectrode systems are used extensively in research and are so named because their dimensions are on the micrometre scale. Such microelectrode systems provide very high field gradients and diffusion characteristics due to their small size. In addition, these types of microelectrode systems have found some limited commercial utility in biomedical applications and are typically used in, for example, blood gas analysis.

Reliable operation of microelectrode systems for preparative electrochemistry and electroanalytical techniques depends critically upon their geometry and the reproducibility of their manufacture. The performance of such a system generally improves as the dimensions of the system are reduced which is why microelectrode and even nanometre scale microelectrode systems are often desirable.

A disadvantage of known microelectrode systems of this type is that the reproducibility and reliability of the fabrication process and the geometries which may be adopted become more limited as the scale is reduced.

The present invention seeks to provide an improved microelectrode system which is more straightforwardly and reproducibly manufactured irrespective of dimensionality.

Thus viewed from one aspect the present invention provides a microelectrode system comprising a laminated structure having at least one conducting layer capable of acting as an electrode, at least one dielectric layer, an aperture formed in the laminated structure, and contact means for allowing electrical contact with at least one conducting layer.

As the dimensions of the microelectrode system of the invention are extremely small, the fields generated within the laminated structure are exceptional and enable highly efficient measurement and/or modification of materials entering into or passing through the system. The laminated structure is simple to manufacture to extremely high tolerances. In addition, the structure has extremely low dead volume thereby considerably simplifying physical sampling regimes.

The aperture may be in the form of a hole which extends through the laminated structure and is open at both ends. Alternatively, the aperture may be in the form of a well having an open end and an opposite end being closed to form a well bottom. In both embodiments, the internal wall of the hole or well formed in the microelectrode system may be uniform (eg substantially tubular) or non-uniform to provide non-uniform fields if desired. Materials may be passed into or through the laminated structure (via the aperture) where inter alia synthesis, analysis or sequencing as desired takes place.

The microelectrode system of the invention may comprise a plurality of apertures (eg holes or wells) formed within the laminated structure and spaced apart from one another. Each hole or well may be individually addressable, in which case each hole or well may have a different function. Alternatively, groups of holes or wells (or the totality of the holes or wells) in a structure may be addressed in parallel thereby enabling amplification of signals and parallel material processing. This latter system may be suitable for larger scale synthetic applications.

In one embodiment, the microelectrode system comprises at least one pair of substantially collinear wells having a common closed end. Particularly preferably, the microelectrode system comprises a plurality of such pairs.

At least one conducting layer of the microelectrode system of the invention acts as an electrode on the internal wall of the hole or well. The or each electrode may be treated to provide appropriate functionality (eg pH measurement or surface treatment for electro-catalysis) by known chemical and/or electrochemical and/or physical modification techniques.

The laminated structure may comprise a plurality of conducting and a plurality of dielectric layers. Preferably consecutive conducting layers are separated, by dielectric layers. Particularly preferably, a dielectric layer is uppermost in the laminated structure. In one embodiment, the laminated structure preferably comprises three conducting layers. Electrical fields are generated between the layers forming the laminated structure and within the aperture to provide the desired conditions.

Typically, the electrodes are formed from a noble metal, preferably gold. Gold may be sputtered onto a polymer which is capable of acting both as the mechanical support and as the dielectric layer. Any form of polymer or other dielectric material which is capable of acting as a support may be used such as for example polyethylenetetraphthalate (PET). Other specialised materials such as ion exchange polymers (eg cation doped polystyrene sulphonate) may be used for specialised applications.

Advantageously, the or each dielectric layer is made from a rubbery material. A suitable material is a polymer which swells when molecules of (for example) water enter the solid state matrix. During use of the microelectrode system, the rubbery dielectric layers separating pairs of conducting layers swell thereby changing the inter-electrode distance. Thus, the interspaced electrodes may be interrogated to determine the degree of swelling of the dielectric layers as a function of the measured resistance.

In more complex systems, material may be grown between the or each conducting layer and the or each rubbery dielectric layer, and the stress placed on the material as a consequence of the swelling of the or each dielectric layer may be measured.

A reagent loaded or functionalised dielectric layer may be used to provide additional functionality by providing ions or other materials to ensure the reproducible behaviour of subsequent systems within the structure. Ions may be conveniently provided by ion exchange resin materials. Other matrices could be employed to provide co-factors for biosensors, etc.

A specialised dielectric layer may also be used. The specialised layer may be in the form of an ion exchange resin, gel or solid electrolyte. In such a system, mass transport from one lateral region of the structure to another may be effected by inter alia osmosis, electro-osmosis, electrophoresis, electrochromatography or ion migration. Reverse flow and counter current techniques may be employed to effect changes in process flows including inter alia deionisation.

The laminated structure may be built on silicon. This has the advantage of being optically flat. Alternatively, the laminated structure may be built on a polymeric material (eg a polymeric material comprising one or more polymers).

The layers forming the laminated structure may be laid down using any one of a number of known techniques including casting, spinning, sputtering or, vapour deposition methods. The aperture may be mechanically or chemically introduced into the laminated structure. Advantageously, a micron gauge wire made of (for example) silver may be introduced into the laminated structure which wire may be etched out once the laminar structure has been completed.

Alternatively, lithographic techniques or physical techniques such as laser oblation and neutron annihilation may be used. It is possible to produce highly uniform electrode layers with precise separations using such techniques allowing highly reproducible functional structures to be achieved.

The microelectrode system of the invention has many applications. For example, it may be used in the deionisation of a solution positioned on one side of a membrane forming the closed end of a well. In such a case, ions may be pumped through the microelectrode system as a consequence of a potential difference applied to electrodes on either side of the common well bottom. In such a case, the well bottom may be conveniently formed from an ion exchange material. The microelectrode may also be used in preparative electrochemistry, electroanalysis and chromatography or other separation techniques. It may also be used as a sensor.

Where the aperture is in the form of a through hole, the microelectrode system according to the present invention may be used in preparative electrochemistry. In such a case, the reactants on one side of the electrode structure are passed through the hole using (for example) a pressure gradient. As they pass through the holes, the reactants are modified by the applied electric field within each hole, either producing the product directly or generating intermediates which undergo further reaction to form the desired product.

If, for example, the microelectrode system was required to have biological functionality for use in an enzyme or antibody system, the electrodes may be formed from metal treated with an organic conducting layer to prevent the activity of the biological agent from being destroyed.

A silver conducting layer may be used which itself may be chloridised to form a silver/silver chloride reference electrode if desired.

The dimensions of the layers and hole or well forming the microelectrode system may be tailored as desired. The precise dimensions of the microelectrode system depend upon the materials used and the techniques employed to form the microelectrode system.

The diameter of the hole or well is typically in the range 0.5 to 500 microns, preferably 1 to 200 microns, particularly preferably 2 to 30 microns, especially preferably about 5 microns.

The thickness of the or each dielectric layer may be in the range 0.5 to 10000 microns, preferably 0.5 to 1000 microns, particularly preferably 1 to 1000 microns, especially preferably 1 to 60 microns, more especially preferably 1 to 10 microns. Where the dielectric is uppermost or intermediate in the laminated structure, the thickness is typically about 5 microns. Where the dielectric is on the base of the laminated structure, the thickness is typically about 55 microns.

The thickness of the or each conducting layer may be in the range 0.5 to 500 microns, preferably 1 to 100 microns, particularly preferably 1 to 10 microns, especially preferably about 3 microns.

At a location remote from the hole or well is provided a means to enable electrical contact with the or each of the conducting layers. One such means of providing electrical contact would be to slice back the outer edges of the dielectric layers thereby exposing the extreme ends of each of the conducting layers. These exposed ends allow electrical contact to be made.

When a microelectrode system according to the present invention is used in a mass transport system, the potential difference created causes diffusion of desired chemical species to the hole or well. In some cases (for whatever reason) this process is slow and the mass transport may be aided through use of inter alia a piezo-electric vibrator or an ultrasonic probe. Mass transport may be additionally controlled (where required) by conventional macroscopic means used in electrochemistry. These techniques include membrane and diffusion, wall jet/wall pipe techniques, rotation, vibration, etc. In the case of a microelectrode system having a through hole, the mass flow may additionally be controlled using differential pressure techniques.

The microelectrode system according to the invention may be in the form a substantially one-dimensional array (eg a tape) or a multi-dimensional array (eg a sheet or more complex matrix) to enable repeated measurements with single use systems.

Preferably, the microelectrode system of the invention further comprises a microheater structure incorporated into the system to control local conditions. Preferably, the microheater is in the form of a resistive element laid down using known semi-conductor techniques. The resistive element may provide localised heating.

The invention will now be further described by way of example only with reference to the accompanying drawings in which;

FIG. 1a is a schematic representation of an microelectrode system according to the invention incorporating a well;

FIG. 1b is a schematic representation of an microelectrode system according to the invention incorporating a through hole;

FIG. 2a is a schematic representation of an microelectrode system according to the invention having three electrodes and incorporating a well;

FIG. 2b is a schematic representation of an microelectrode system according to the invention having three electrodes and incorporating a through hole;

Figure 5A:
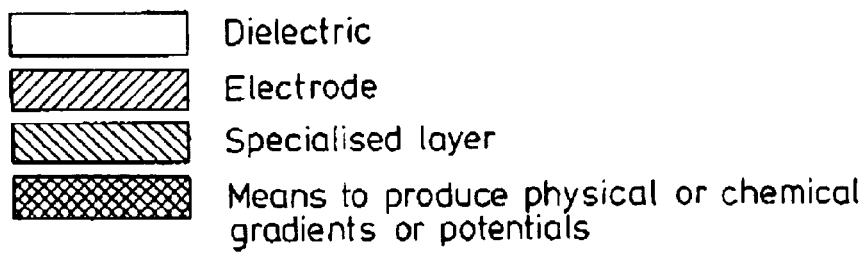
Figure 5A:
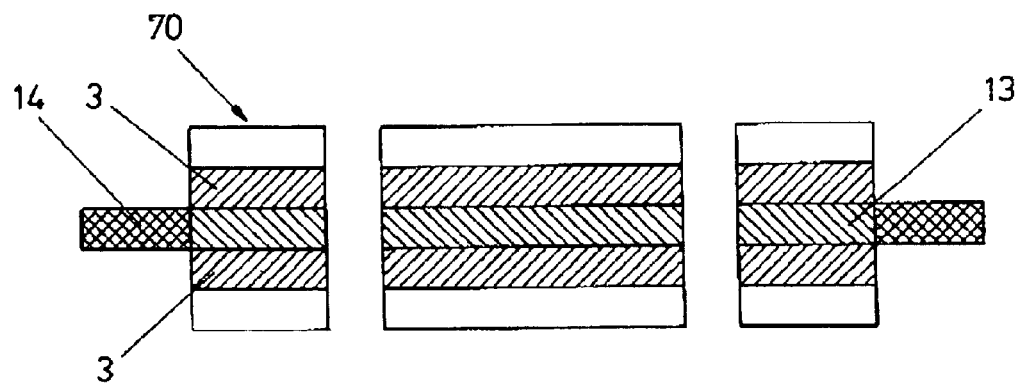
Figure 6:
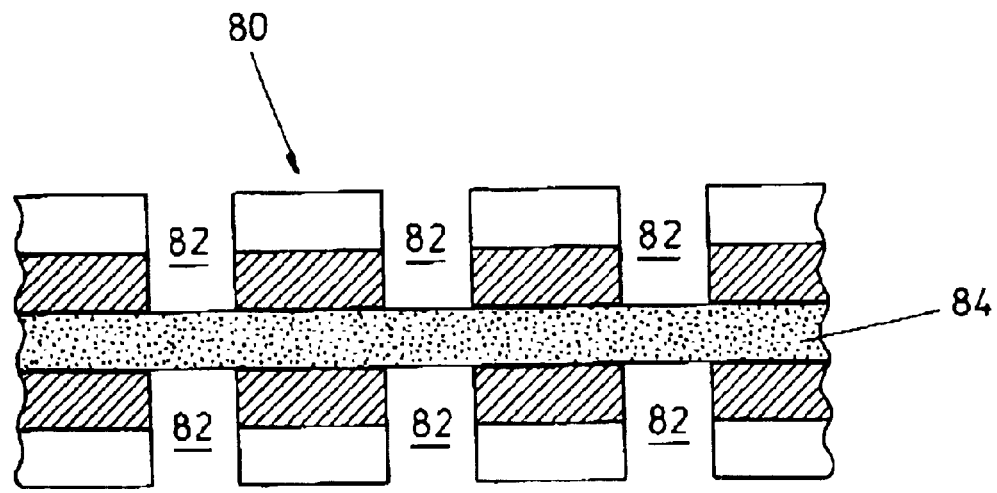
Figure 7:
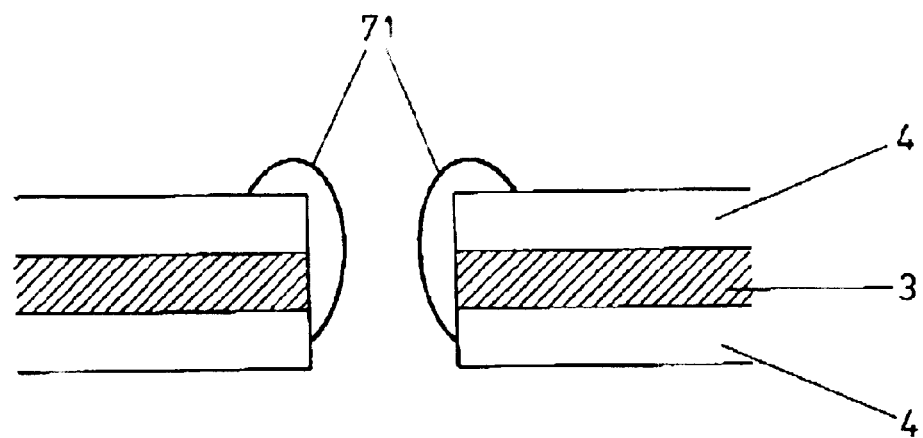
Figure 8A:
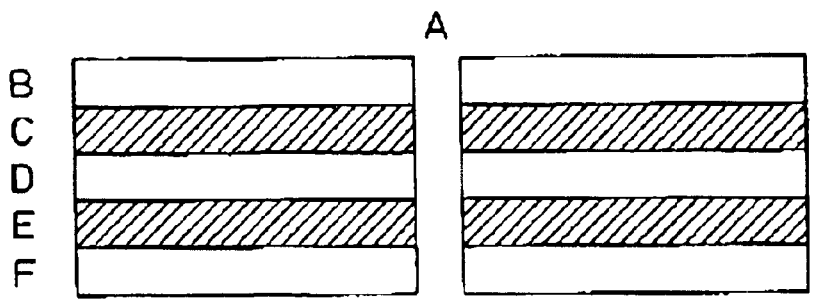
Figure 8B:
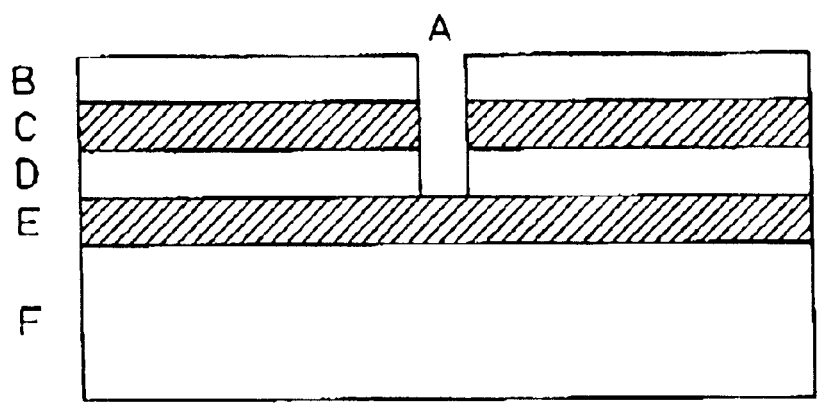

FIGS. 5a (side elevation) and 5b (plan) are schematic representations of an microelectrode system according to the invention incorporating a specialised or functionalised layer structure;

FIG. 6 is a schematic representation of a microelectrode system according to the invention forming a membrane transport system;

FIG. 7 is a schematic representation of a microelectrode system according to the invention forming an impedance imaging system; and FIGS. 8a and 8b illustrate preferred embodiments of microelectrodes of the invention.

Referring to FIG. 1a, a microelectrode system 1 comprises alternating layers of conductor 3 and dielectric (or insulator) 4. The laminated structure 2 comprises two conductor layers 3 and two dielectric layers 4 formed on a base 5 of silicon or a polymeric material. The conducting layers 3 form electrodes in the microelectrode system 1. The laminated structure has formed within it an aperture in the form of a well 6 being open at one end 7 and closed at the opposite end 8.

The microelectrode system 10 shown in FIG. 1b has formed within the laminated structure 2 a through hole 11 and comprises three dielectric layers 4 and two conducting layers 3.

Figure 3:
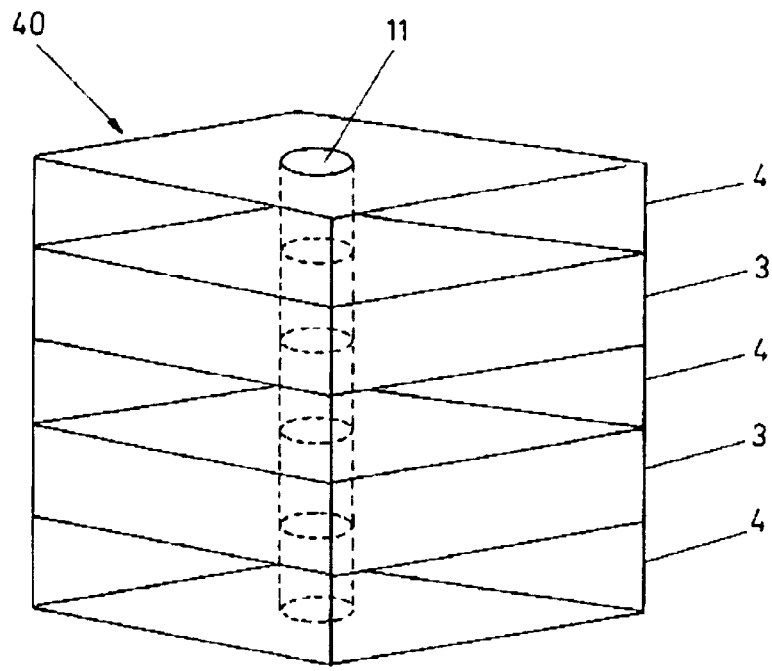
FIG. 3 is a schematic three-dimensional representation of an microelectrode system according to the present invention incorporating two electrodes and a through hole.

FIGS. 2a and 2b illustrate microelectrode systems 20 and 30 respectively which are similar to the microelectrode systems 1, 10 with similar reference numerals retained to avoid confusion. Each of the microelectrode systems 20, 30 comprises three conducting (electrode) layers 3 and three dielectric layers 4. Hole 11 (FIG. 2b) or well 7 (FIG. 2a) define an internal wall formed from alternating layers of insulating and conducting material. This produces a circular micro-band microelectrode system in the form of a uniform tube. This can be seen more clearly with reference to FIG. 3 which is a three-dimensional representation of the microelectrode system 10 of FIG. 1b.

Figure 4A:
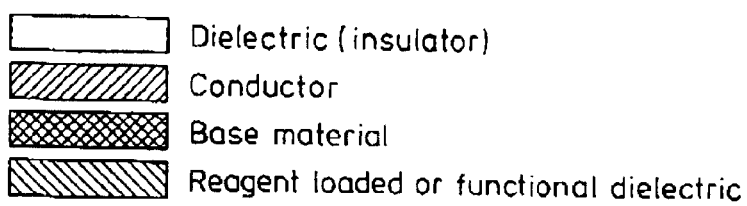
FIG. 4a is a schematic representation of an microelectrode system according to the invention incorporating two electrodes, a reagent-loaded or functionalised dielectric and a well.
Figure 4A:
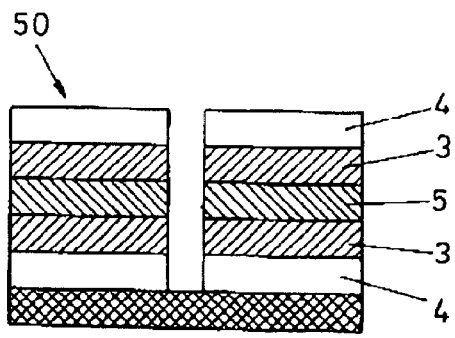
Figure 4B:
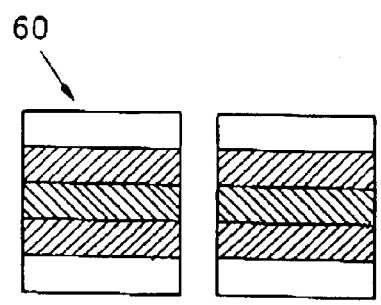
FIG. 4b is a schematic representation of an microelectrode system according to the invention incorporating two electrodes, a reagent loaded or functionalised dielectric, and a through hole.

Materials passing into the structure may be pre-treated. A system suitable for pretreatment of material is shown in FIGS. 4a and 4b (where parts equivalent to those in FIGS. 1a and 1b have been given equivalent reference numerals). The microelectrode systems 50, 60 contain two electrode layers 3, two dielectric layers 4 and a reagent loaded or functionalised dielectric layer 5. The reagent loaded or functionalised dielectric layer 5 is able to provide additional functionality by providing ions or other materials to ensure the reproducible behaviour of subsequent systems within the structure. Ions could be provided by ion exchange resin materials. Other matrices could be employed to provide co-factors for biosensors, etc. The layer 5 could act as a buffer if, for example, there was some kind of ion exchange taking place where a remote reservoir was replenishing the ions exchanged within the medium in contact with the membrane.

Figure 5B:
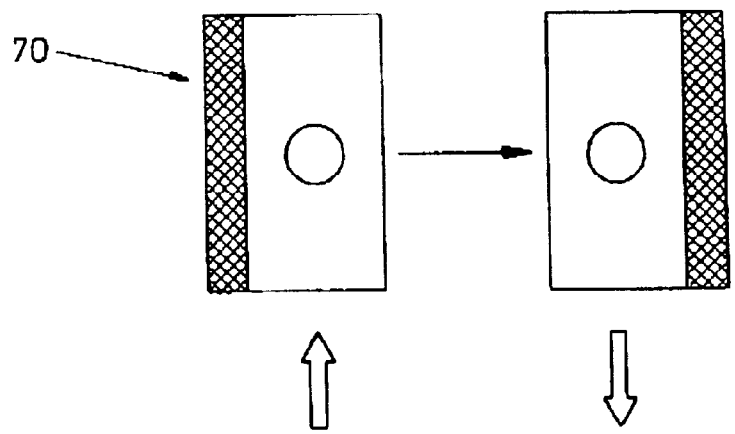

Referring now to FIGS. 5a and 5b a microelectrode system according to the invention is designated generally by the reference numeral 70 with parts equivalent to those shown in FIG. 1b given equivalent reference numerals. The microelectrode system 70 comprises a specialized layers 13 between two electrode layers 3. The system further comprises means 14 to produce physical or chemical gradients or potentials to the specialized layer 13. The specialized layer 13 may be in the form of an ion exchange resin, gel or solid electrolyte. In such a system 70 mass transport from one lateral region of the structure to another may be effected by, for example, osmosis, electro-osmosis, electrophoresis, electrochromatography, ion migration, etc. Reverse flow and counter current techniques may be employed to effect changes in process flows including inter alia deionization.

In FIG. 6, a microelectrode system 80 suitable for use in deionisation of a solution is designated generally by the reference numeral 80. The microelectrode system 80 comprises a plurality of wells 82. Each of the wells 82 is split into pairs by the presence of a continuous layer 84 which serves as a common well bottom for each pair. The well bottom is formed from an ion exchange material. Electrodes on either side of the well-bottom generate a potential gradient which forces ions to move across the membrane. This system may be used to deionise water.

FIG. 7 illustrates a microelectrode system suitable for impedance imaging (eg mammography). It comprises alternating conducting 3 and dielectric layers 4 with a gold overplating 71 which is contactable with the skin for example. It is not important in this embodiment for the overplating material to contact in the centre of the hole. The overplating adopts a shape according to local variations in the environment. Provided the plating extends beyond the hole or well to the upper surface thereby allowing electrical contact to be made with an external surface, the shape and size is not critical. The overplating may be applied by standard electroplating methods (electrochemical methods).

FIGS. 8a and 8b illustrate embodiments of the invention of the hole-type and well-type respectively. Dielectric layers are made from poly(ethylenetetraphthalate) and conducting layers from gold. The detailed construction of each embodiment is given in the following tables (typical ranges are given for illustrative purposes only):

1) Hole Structure (FIG. 8a)
   Dimensions (in microns):

| Description | Letter | Dimension | Typical Range |
| --- | --- | --- | --- |
| Aperture | A | 5 | 0.5–500 |
| First dielectric layer | B | 5 | 1–1000 |
| First conducting layer | C | 3 | 0.5–500 |
| Second dielectric layer | D | 5 | 0.5–1000 |
| Second conducting layer | E | 3 | 0.5–500 |
| Third dielectric layer | F | 5 | 1–1000 |

2) Well Structure (FIG. 8b)
   Dimensions (in microns):

| Description | Letter | Dimension | Typical Range |
| --- | --- | --- | --- |
| Aperture | A | 5 | 0.5–500 |
| First Dielectric layer | B | 5 | 1–1000 |
| First conducting layer | C | 3 | 0.5–500 |
| Second dielectric layer | D | 5 | 0.5–1000 |
| Second conducting layer | E | 3 | 0.5–500 |
| Third dielectric layer | F | 55 | 1–10000 |

What is claimed is:

1. A microelectrode system comprising a laminated structure having:
   at least one conducting layer of thickness in the range 1 to 10 microns capable of acting as an electrode,
   at least one dielectric layer, at least one of which is made from a rubbery material having a solid state matrix capable of swelling in the presence of a liquid or gas;
   an aperture formed in the laminated structure with a diameter in the range 0.5 to 500 microns, wherein said aperture is a through hole which extends through the laminated structure and is open at both ends; and
   contact means for allowing electrical contact with at least one conducting layer.

2. A microelectrode system as claimed in claim 1 wherein said aperture defines a uniform or non-uniform internal wall in the laminate structure.

3. A microelectrode system as claimed in claim 1 wherein said aperture defines a substantially tubular internal wall in the laminate structure.

4. A microelectrode system as claimed in claim 1 comprising a plurality of apertures.

5. A microelectrode system as claimed in claim 1 wherein at least one conducting layer is functionalised.

6. A microelectrode system as claimed in claim 1 wherein consecutive conducting layers are separated by dielectric layers.

7. A microelectrode system as claimed in claim 1 wherein the laminate structure is constructed on a base comprising silicon or a polymeric material.

8. A microelectrode system as claimed in claim 1 wherein at least one conducting layer is metallic and treated with an organic conducting layer.

9. A microelectrode system as claimed in claim 1 wherein at least one conducting layer is a silver/silver chloride reference electrode.

10. A microelectrode system as claimed in claim 1 wherein at least one conducting layer consists essentially of gold.

11. A microelectrode system as claimed in claim 10, wherein at least one dielectric layer is polymeric and acts as a support for the gold conducting layer.

12. A microelectrode system as claimed in claim 1 comprising means for assisting mass transport.

13. A microelectrode system as claimed in claim 12 wherein said means for assisting mass transport is a piezoelectric vibrator or ultrasonic probe.

14. A microelectrode system as claimed in claim 1 comprising alternating conducting and dielectric layers.

15. A microelectrode system as claimed in claim 1 wherein at least one dielectric layer comprises a specialized layer in the form of an ion exchange resin, gel or solid electrolyte.

16. A microelectrode system as claimed in claim 15 wherein the specialized layer is provided with means to apply physical or chemical gradients or potentials thereto.

17. A microelectrode system as claimed in claim 1 wherein at least one dielectric layer comprises a reagent loaded or functionalised layer.

18. A microelectrode system comprising a laminated structure having:
   at least one conducting layer capable of acting as an electrode, wherein said conducting layer is metallic and comprises an organic conducting layer
   at least one dielectric layer,
   an aperture formed in the laminated structure, and
   contact means for allowing electrical contact with the at least one conducting layer.

19. A microelectrode system comprising a laminated structure having:
   at least one conducting layer capable of acting as an electrode;
   at least one dielectric layer,
   an aperture formed in the laminated structure, and
   contact means for allowing electrical contract with the at least one conducting layer,
   said system comprising means for assisting mass transport being a piezoelectric vibrator or ultrasonic probe.

20. A microelectrode system comprising a laminated structure having:
   at least one conducting layer capable of acting as an electrode,
   at least one dielectric layer, wherein at least one of said at least one dielectric layers comprises a specialised layer in the form of an ion exchange resin, gel or solid electrolyte and said specialised layer is provided with means to apply physical or chemical gradients or potential thereto,
   an aperture formed in the laminated structure, and
   contact means for allowing electrical contact with the at least one conducting layer.

* * * * *